United States Patent [19]

Johnson et al.

[11] Patent Number: 5,429,726
[45] Date of Patent: Jul. 4, 1995

[54] METHODS FOR REDUCING LEVEL OF INTERFERANTS IN BIOSENSOR SYSTEMS AND SOLUTIONS USED IN THESE METHODS

[75] Inventors: Jay M. Johnson, Dayton; Robert B. Spokane, Bellbrook, both of Ohio

[73] Assignee: The Yellow Springs Instrument Company, Inc., Yellow Springs, Ohio

[21] Appl. No.: 271,006

[22] Filed: Jul. 5, 1994

Related U.S. Application Data

[63] Continuation-in-part of Ser. No. 56,358, Apr. 30, 1993, abandoned.

[51] Int. Cl.⁶ .............................................. G01N 27/26
[52] U.S. Cl. .................... 204/153.12; 204/153.1; 204/403; 435/817
[58] Field of Search ............... 204/153.1, 153.12, 403; 435/817

[56] References Cited

U.S. PATENT DOCUMENTS 4,855,353  8/1989  Kurami et al. ..................... 525/54.1

*Primary Examiner*—John Niebling
*Assistant Examiner*—Bruce F. Bell
*Attorney, Agent, or Firm*—Biebel & French

[57] ABSTRACT

Improved methods and compositions are provided to inhibit interference from formaldehyde in polarographic analytic methods. In the enzymatic oxidation of methanol to hydrogen peroxide and formaldehyde, formaldehyde serves as an interfering agent in systems where the oxygen consumed or the hydrogen peroxide produced is polarographically measured. To inhibit this interference, an amine-containing formaldehyde scavenger is added to the test system. Preferably, the scavenger comprises a polyalkyleneimine such as polyethyleneimine having a molecular weight of between about 200–1,000,000 amu. The invention is particularly well-suited for use in polarographic analytical apparatus wherein laminated membrane type enzyme electrodes are used to perform amperometric measurement with alcohol oxidase enzyme used as the oxidoreductase enzyme. Determination of methanol concentration in liquid samples can be used to assess the amount of L-Asp-L-Phe-methyl ester (aspartame-TM) present in diet soft drink samples that have been hydrolyzed with the enzyme Bovine alpha-chymotrypsin to yield L-Asp-L-phe and methanol.

15 Claims, 8 Drawing Sheets

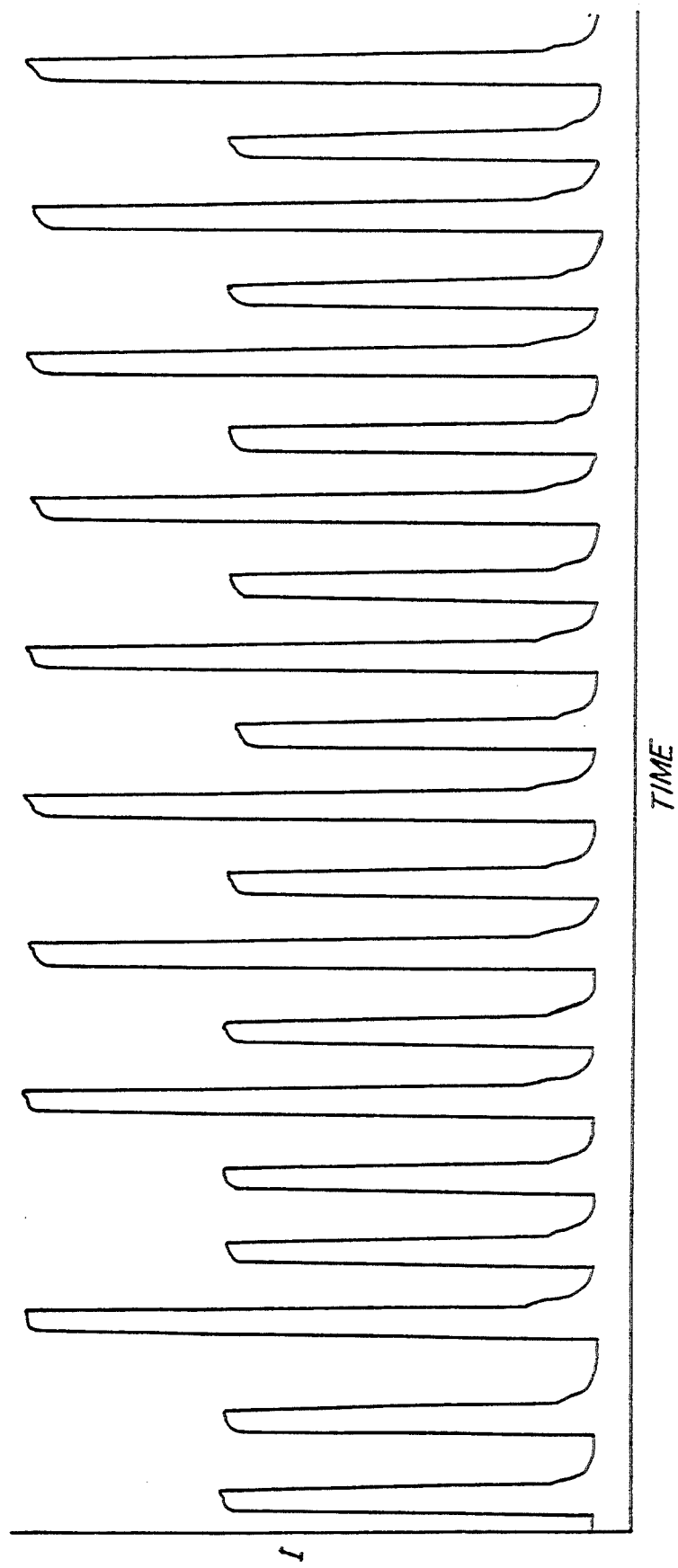

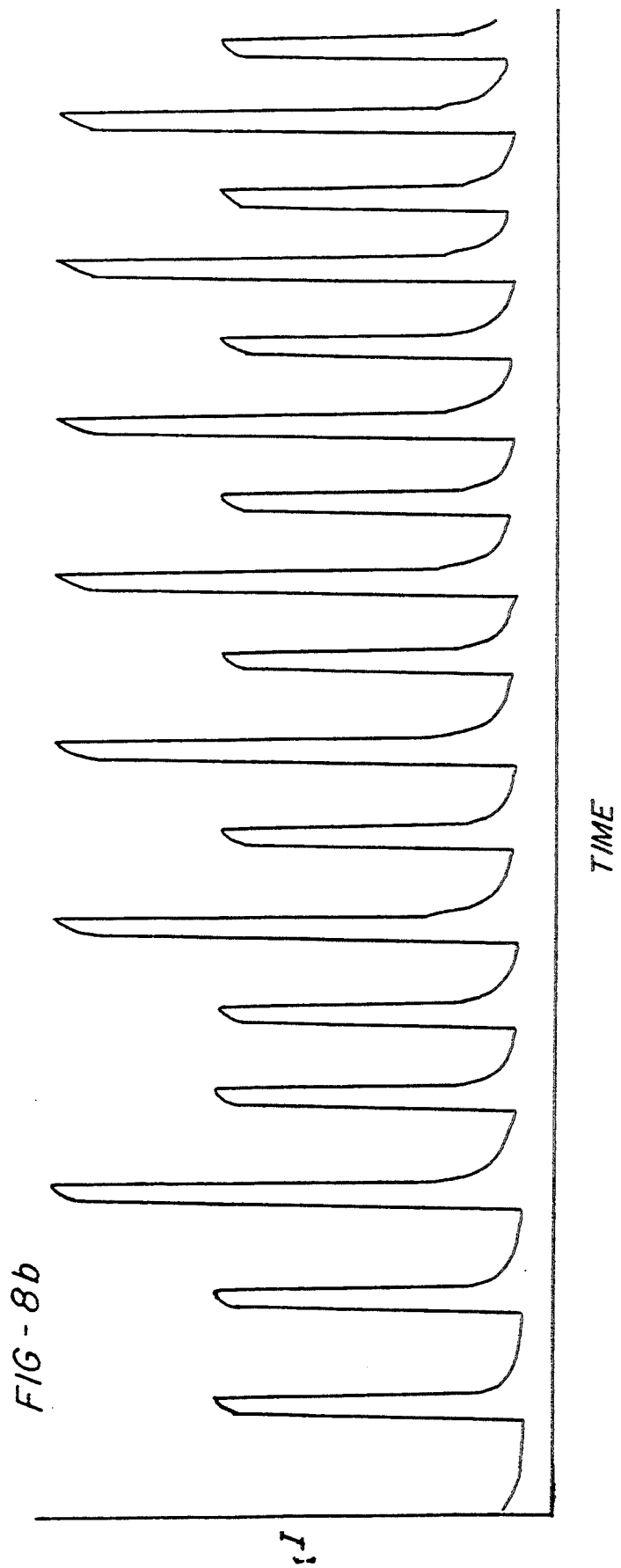

METHODS FOR REDUCING LEVEL OF INTERFERANTS IN BIOSENSOR SYSTEMS AND SOLUTIONS USED IN THESE METHODS

CROSS REFERENCE TO RELATED APPLICATIONS

This application is a Continuation-In-Part of application Ser. No. 08/056,358, filed Apr. 30, 1993 now abandoned.

FIELD OF THE INVENTION

The present invention pertains to improved methods of measuring analyte concentrations in liquid samples and to improved liquid buffer solutions that are to be used in those methods. The invention, more specifically, is directed to analyte concentration detection systems wherein polarographic measurement is taken of the analyte itself, or of a reaction product of or a reactant consumed by an enzymatic reaction with the analyte.

BACKGROUND OF THE INVENTION

Polarographic cell systems have met with wide acclaim particularly in the medical field, providing for detection and concentration measurement of many desired analytes. Enzymes are commonly used in such systems, especially in those situations wherein the analyte itself is not polarographically active but where a reaction product formed or reactant consumed by an enzymatic reaction with the analyte is polarographically active.

For example, in medical applications, one common procedure is to measure glucose in the blood of a patient. Typically, blood samples are withdrawn from the patient for an in-line analysis for glucose concentration using a glucose oxidase electrode with a polarographic detector for detecting $H_2O_2$ generated in accordance with the reaction:

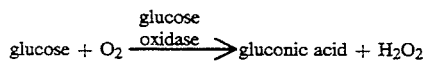

The hydrogen peroxide generated by the reaction is measurable by a polarographic detector and, by appropriate calibration and calculation, glucose content in the sample can be accurately determined by the $H_2O_2$ formed in the reaction.

Other areas in which analyte detection is required abound. For example, other biological detection systems, drug detection systems, chemical process systems, including fermentation systems and others, all require precise measurement of a variety of analytes. One specific example is now seen in the diet soft drink bottling industry where the artificial sweetener, aspartame (N-L-a-aspartyl-L-phenylalanine-methyl ester), commonly known by the brand name "Aspartame", has become the sweetening agent of choice.

Soft drink bottlers must determine the sweetener level present in a multiplicity of syrup or precursor diet soft drink lots to serve as an indication of the amount of water they must add to the syrup to obtain acceptable soft drink formulations as dictated by the syrup manufacturers. Additionally, once the desired dilution of the syrup has been made, the bottlers often check sweetener concentration to ensure compliance with desired sweetener concentration ranges.

One present method utilized to determine "aspartame" concentration levels is to chemically cleave the methyl ester functional moiety from the N-L-a-aspartyl-L-phenylalanine-methyl ester molecule via chymotrypsin enzymatic reaction. The reaction proceeds as follows:

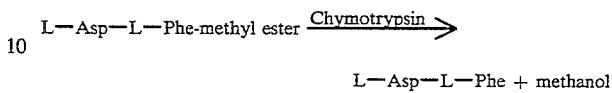

The amount of methanol produced can then be polarographically determined in known enzymatic analysis systems by use of the following equation, with the $H_2O_2$ produced being polarographically measured

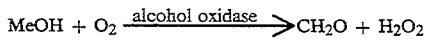

Polarographic determination of the $H_2O_2$ produced can, for instance, be made in polarographic cells of the type disclosed in U.S. Pat. Nos. 3,979,274 and 4,073,713 (Newman), both patents being hereby incorporated by reference herein.

In accordance with these known polarographic cell structures, a laminated enzyme membrane is provided in which the innermost membrane of the laminate is located adjacent the working electrode of the polarographic detection circuit. Higher weight molecular species are prohibited from passing through this innermost membrane so that they will not contact the working electrode, while the polarographically active substance, $H_2O_2$, can permeate the membrane and contact the electrode.

One obstacle which inhibits application of the Newman laminated enzyme membrane approach to methanol concentration measurement is that the $CH_2O$ produced as a result of the alcohol oxidase (AOX) catalyzed oxidation of methanol interferes with accurate determination of the $H_2O_2$ at the working electrode. Possibly, the $CH_2O$ produced at the enzyme site competes with MeOH for reaction with the enzyme or the $CH_2O$ itself produced may directly interfere with current measurement at the working electrode surface.

Undesirable instrument responses were found when $H_2O_2$ polarographic detection methods were used in Newman type laminated enzyme membrane systems with alcohol oxidase used as the catalytic enzyme. These responses included drooping or ramping of current measurement plateaus as recorded on strip chart recorders used in conjunction with the measurement equipment, especially at higher MeOH concentrations and slow return of the analytical equipment to an acceptable baseline current after analyte sample injection.

Accordingly, there is a need in the assay field to provide improved, more accurate analysis in those measurement systems wherein formaldehyde exists as a possible interferant.

There is a more specific need to provide for improved polarographic detection in laminated enzyme membrane systems of the Newman type described above wherein $CH_2O$ present or formed in the system interferes with accurate polarographic measurement at the transducer.

SUMMARY OF THE INVENTION

In accordance with the above, the present invention is directed to methods and compositions for minimizing interference with transducers, such as polarographic or amperometric sensors, caused by the presence of formaldehyde present in the system as a reactant or reaction product We have found that addition of an effective amount of a $CH_2O$ scavenger into such test systems improves the accuracy and performance of the test system. Although we are not to be bound by any particular theory of operation, it is thought that the scavenger serves to react with the $CH_2O$ present to produce a non-interfering product molecule, rendering the $CH_2O$ less available to interfere with the desired reaction and operation of the analytic method.

More specifically, in a laminated enzyme membrane polarographic system of the Newman electrode type, alcohol oxidase (AOX) is employed as the catalytic enzyme in a reaction system designed to make amperometric measurement of $H_2O_2$ at a working electrode in accordance with the reaction:

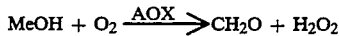

$$MeOH + O_2 \xrightarrow{AOX} CH_2O + H_2O_2$$

The current measured at the working electrode is proportional to the amount of $H_2O_2$ produced during the enzymatic reaction. $H_2O_2$ gains access to the working electrode through the innermost membrane of the enzyme containing laminated membrane assembly. This current measurement is correlated to the amount of MeOH present in the test sample. In turn, MeOH concentration correlates to the amount of aspartame sweetener (i.e., L-Asp-L-Phe-methyl ester) present. As explained above, in a precursor reaction, the methyl ester moiety of the "aspartame" molecule is cleaved via catalytic reaction with chymotrypsin to form L-Asp-L-Phe and MeOH.

In these systems, it is desirable to contact the $CH_2O$ interferant with a formaldehyde scavenger comprising an amine-containing polymeric moiety having a molecular weight between about 200–1,000,000. It is postulated that the amine groups react with the $CH_2O$ available in the system, thereby rendering same less prone to Interfere with: (1) the desired oxidation of MeOH by the AOX enzyme, or (2) the electrochemical reaction of $H_2O_2$ at the working anode. Most probably, the amine groups react with the $CH_2O$ in the system to form a Schiff Base.

The invention will be further described in conjunction with the following detailed description and appended drawings.

IN THE DRAWINGS

FIG. 8a is a schematic illustration of a strip chart showing instrument response curves for alternate injections of differing MeOH analyte concentration levels when the polarographic cell contains a formaldehyde scavenger; and FIG. 8b is a schematic illustration of a strip chart showing instrument response curves for alternate injections of differing MeOH concentration levels in instances where the polarographic cell does not contain formaldehyde scavenger.

DETAILED DESCRIPTION OF THE PREFERRED EMBODIMENT

Figure 1:
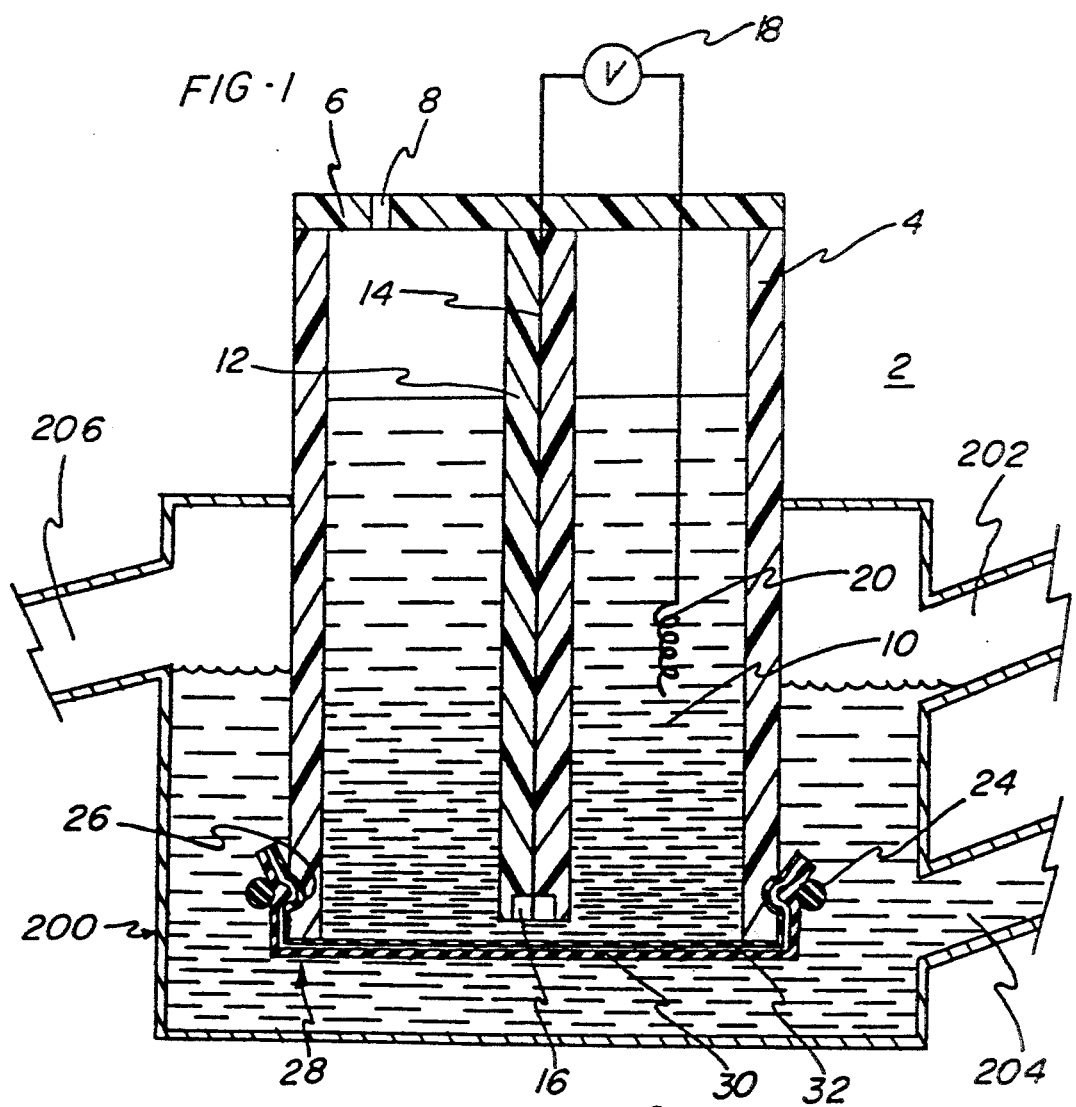
FIG. 1 is a vertical section view of a polarographic cell that may be used in accordance with the invention.

Turning now to FIG. 1 of the drawings, there is schematically shown a polarographic cell 2 of the type that may be incorporated in industrial analyzers, such as the Model 27 and/or Model 2700 analyzers available from The Yellow Springs Instrument Company, Inc., Yellow Springs, Ohio.

These analyzers comprise a Newman type laminated enzyme assembly as described more specifically hereinafter. Polarographic cell 2 includes an electrically insulating container 4 composed of suitable dielectric, such as glass or plastic. Container 4 is covered by electrically insulating cap 6 which, as shown, includes aperture 8 through which electrolyte 10 is admitted to the cell.

Electrically insulating rod or column 12 extending downwardly into the cell from cap 6 is provided with conductor 14 that at the distal end thereof is connected to working or sensor electrode 16 that may be composed of platinum, gold, silver, graphite or the like. The proximal end of conductor 14 is connected with DC voltage source 18.

Reference electrode 20 is provided between the column 12 and the walls of container 4. Electrode 20 may comprise silver chloride coated silver wire. Electrolyte 10 fills the space between reference electrode 20 and working electrode 16.

The lower end of the container 4 is provided with a snap in O-ring 24 snap fit into annular groove 26 on the outer wall of container 4 to hold laminated enzyme containing membrane 28 securely in fluid tight relation over the bottom of container 4.

Surrounding the bottom portion of polarographic cell 2 is reservoir 200 adapted to contain analyte containing solution or buffer as shall be explained in more detail hereafter. Reservoir 200 includes analyte injection channel 202, and buffer injection channel 204 Overflow weir 206 provides for overflow to drain from the system.

In accordance with conventional techniques available, for example in conjunction with automated analyzers, such as the Model 2700 available from The Yellow Springs Instrument Company, Inc., the analyte containing sample is injected into channel 202 so that it will contact the laminated enzyme-containing membrane 28. Buffer solution is fed through channel 204 so as to dilute the analyte sample to the desired working ratio for the measurement (e.g., 20–30:1 by volume buffer:analyte solution). Also, and in accordance with the operation of the Model 2700, after measurement of an analyte sample has been made, reservoir 200 is flushed with buffer solution to wash liquid from the previous measurement away from contact with the laminated enzyme-containing membrane 28 so as to be eliminated from the system flowing over weir 206. Meanwhile, the amperage is still measured at the working or sensor electrode 16.

Additional analyte sample will not be drawn through channel 202 until such time as a predetermined baseline current value has been obtained during the flushing cycle so as to ensure the accuracy of the measurements. In this regard, it is common to set the microprocessor controls on the Model 2700 analyzer so that fresh analyte sample will not be drawn through injection channel 202 until the amperage measured at 16 during this flushing cycle is within 2% of the preceding baseline current.

Figure 2:
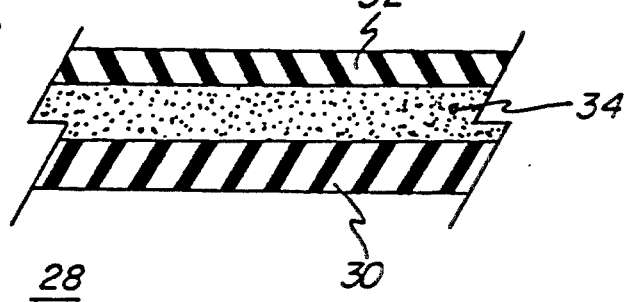
FIG. 2 is an enlarged view of a cross-section of an enzyme containing laminated membrane which may be used in accordance with the inventive methods hereof.

As best shown in FIG. 2, the laminated membrane 28 comprises outer support/barrier layer 30 in contact with the liquid containing the desired analyte, and an inner membrane layer 32 adjacent the electrolyte 10 in container 4 and in close proximity to working electrode 16. As shown, an oxidoreductase enzyme 34 is stably positioned intermediate membrane layers 30 and 32 although, in accordance with conventional techniques, such as those disclosed in U.S. Pat. No. 4,541,666 (D'Orazio et al), the enzyme could be actually incorporated as an immobilized phase in one of the membranes.

When methanol is the desired analyte, alcohol oxidase (AOX) is provided as enzyme 34 in admixture with glutaraldehyde to promote crosslinking so as to immobilize the enzyme.

In polarographic measurements, two electrodes may be used with one of the electrodes being polarized and not allowing current to flow until depolarized by a substance being measured In the cell structure shown in FIG. 1, electrode 20 is the cathode and is not polarized. Electrode 20 is frequently referred to as the reference electrode. The other electrode, electrode 16 as shown in FIG. 1, functions as an anode and is polarized. In the presence of the substances being measured, it becomes depolarized and current flows in proportion to the concentration of the analyte. This electrode is frequently referred to as the sensor or working electrode. The electrodes as shown in FIG. 1 are in electrically insulating relation, and the electrolyte material which occupies cell 4 provides an electrical path between the two electrodes. Typical electrolytes include sodium or potassium chloride. The solvent for such electrolyte may be water, glycols, glycerine, and mixtures thereof.

General principles of polarographic cell operation may be discerned by reading U.S. Pat. No. 3,539,455, which is incorporated by reference herein.

Turning again to FIG. 2, outer support/barrier layer 30 comprises a polycarbonate film having a thickness of from 5 to 7 microns (a nitrogen flow rate of 1–300 ml/min/cm$^2$ at 10 psi) and pore sizes on the order of from about 1–350 A° in diameter. Films for layer 30 are available from Poretics, Inc., Livermore, Calif.

Layer 32 is positioned adjacent working electrode 16 and is essentially composed of homogenous silicone, methyl methacrylate or cellulose acetate. Preferably, layer 32 is cellulose acetate from about 0.5 to 2 $\mu$m in thickness.

Details of the methods by which the laminated membrane is prepared and constructed need not be repeated herein as same are already given in the aforementioned Newman patents.

With regard to the general methods that are employed to determine aspartame levels in diet soft drinks, these are reported in "Artificial Sweeteners—Determination of Aspartame in Beverages Using an Alcohol Oxidase Enzyme Electrode", J. Assoc. of Analytical Chemistry 72, 30–33 (1989). As previously noted in a first, precursor reaction step, the aspartame (L-Asp-L-Phe-methyl ester) is subjected to esterase cleavage. Then, the MeOH produced as a result of this reaction is measured using a laminated enzyme containing membrane as shown in FIGS. 1 and 2 using AOX as the enzyme.

With specific regard again to FIG. 2, outer membrane 30 allows passage of relatively low molecular weight species, such as MeOH therethrough, to gain access to the AOX immobilized between outer membrane 30 and inner membrane 32. Outer membrane 30 serves as a barrier, prohibiting passage of molecules having a mw of about 100,000 or above from gaining access to the enzyme 34.

At the enzyme site, MeOH is catalytically oxidized by AOX yielding $CH_2O$ and $H_2O_2$. The $H_2O_2$ formed in the reaction migrates through inner layer 32 and is oxidized by electrode 16. Amperage then running through the cell is measured and recorded by a strip chart or like recording instrument. Unfortunately, the $CH_2O$ formed interferes with the accuracy and reliability of this measurement.

Inner membrane 32, preferably cellulose acetate membrane serves as a molecular screen to allow low molecular weight materials, such as $H_2O_2$, to gain access to electrode 16, while prohibiting higher molecular weight molecules (i.e., molecules having molecular weights of greater than around 100) from gaining access to the working electrode.

In order to minimize the deleterious effects of $CH_2O$ on the reaction, it is desirable that the formaldehyde scavenger gain access to and function in the enzyme layer. Accordingly, in order to pass through membrane 30, the top end range for the formaldehyde scavenger should be about 1,000,000 a.m.u. The upper end range for the scavenger molecular weight is determined by desired solubility or dispensibility characteristics of the scavenger. At the same time, the formaldehyde scavenger should have a molecular weight greater than about 200 a.m.u. so that it will not pass through membrane 32 to gain access to working electrode 16. Otherwise, it too could adversely affect the desired polarographic measurement.

At present, it is preferred to supply the formaldehyde scavenger as part of the buffer solution that is used to dilute the analyte sample and flush the cell after analyte measurements have been taken. Other mechanisms for providing contact of the formaldehyde scavenger with the enzyme-containing laminated membrane 28 could also be employed. For example, direct injection of the scavenger to the reservoir 200 could be made, or the scavenger could be mixed with the analyte solution itself.

As to the formaldehyde scavenger, this is preferably an amine containing polymer having a molecular weight of between about 200–1,000,000, preferably 200–5,000. The polymer should be soluble or dispersible in the fluid medium contained in reservoir 200 (i.e., the buffer solution plus analyte solution) so as to ensure sufficient contact of the scavenger with the laminated membrane 28.

Based upon presently available data, it is preferred to use a polyalkyleneimine polymer, as the formaldehyde scavenger. More preferably, these polymers are based upon ethyleneimine repeat units having the structure

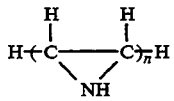

wherein the overall molecular weight of the polymer is between about 200–1,000,000. At present, it is preferred to use poly(ethyleneimine) (PEI) having a molecular weight of 600. This polymer is available from Polysciences, Inc., Warrington, Pa. 18976. It is miscible in water.

The PEI can be supplied to the laminated membrane in a wide variety of concentrations: it is preferred that it should be present in a molar amount greater than or equal to the amount of MeOH present in the analyte samples.

If supplied as part of the buffer solution, it is convenient to provide from $1 \times 10^{-4}$ to $1 \times 10^3$ grams-scavenger/liter. Preferably, when used as part of the buffer solution, the PEI formaldehyde scavenger is present in the buffer solution in an amount of 0.1–100 g/liter. The pH range over which the PEI is effective is very broad although it is most effective at a pH of above about 8. When AOX is the enzyme, practical operating considerations for enzyme performance dictate that the upper pH range should be about 9.5.

Buffer solutions that are presently supplied for use in connection with AOX enzyme containing laminated membranes are adapted to provide a working environment pH (i.e., the pH of the fluid medium in reservoir 200) of between about 8–10. In accordance with the invention, buffer solutions comprising PEI formaldehyde scavenger may also comprise carbonates, phosphates, bicarbonates, acetates, borates, alkali or rare earth salts, organic buffers, bactericides, etc.

One exemplary class of organic buffers that may be employed is commonly referred to as Good's buffers. These are discussed in an article entitled, "Hydrogen Ion Buffers for Biological Research", Analytical Biochemistry 104, 300–310 (1980). These buffers may be generically classified as either aminocarboxylic acid compounds or aminosulfonic acid compounds. Among these buffers, the following are mentioned: poly-L-ornithine; N-[2-hydroxy-1,1-bis(hydroxymethyl)ethyl] glycine; 3-[N-bis(hydroxyethyl)amino]-2-hydroxypropanesulfonic acid; N-hydroxyethylpiperazine-N'-ethanesulfonic acid; N-tris(hydroxymethyl)methylamino-ethanesulfonic acid; N-hydroxyethylpiperazine-N'2-hydroxypropanesulfonic acid; 3-(N-morpholino)-2-hydroxypropanesulfonic acid; piperazine-N,N'-bis(2-hydroxypropanesulfonic acid) dihydrate; 3-[N-tris(hydroxymethyl)methylamino]-2-hydroxypropanesulfonic acid; and N-tris(hydroxymethyl) methylaminoethanesulfonic acid.

The most important characteristic is that the buffer should provide a pH environment of from about 8–10, preferably about 9.

Preferred buffer compositions are as follows:

|  | Preferred Aqueous Solution - 1 liter | Most Preferred Aqueous Solution - 1 liter |
|---|---|---|
| sodium bicarbonate | .7–70 g/l | 7.79 g/l |
| sodium chloride | .3–30 g/l | 3.0 g/l |
| benzoic acid, Na salt | .7–7 g/l | 0.93 g/l |
| sodium carbonate | .05–5 g/l | .76 g/l |
| Dipotassium EDTA | .05–5 g/l | .56 g/l |
| PEI (mw 600) (bactericide) | 0.1–100 g/l | .52 g/l |
| gentamicin sulfate | .7–70 mg/l | 7.4 mg/l |

Although the PEI solutions shown above are aqueous solutions, other carrier liquids, including organic solvents, etc. may be employed. The performance criteria for selection of appropriate carrier liquids include compatibility with the enzyme and the laminated membrane, pH buffer performance, and solubility or dispersibility of PEI formaldehyde scavenger therein.

Figure 3A:
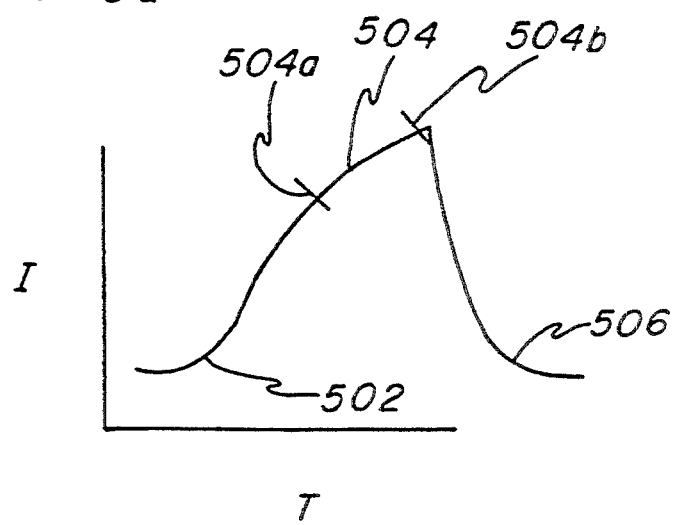
FIG. 3a is a schematic illustration of a strip chart recording of the output of an automatic Newman type polarographic biosensor, displaying the electrical current of a methanol containing sample in the absence of a formaldehyde scavenger.
Figure 3B:
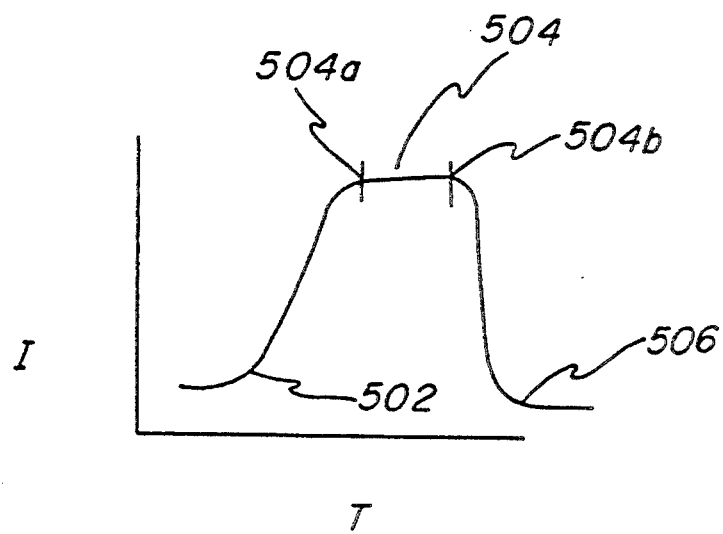
FIG. 3b is a schematic illustration, similar to that of FIG. 3a, except that the polarographic cell contains a formaldehyde scavenger in accordance with the invention.

Turning to FIGS. 3a and 3b, there are schematically shown strip charts that would be generated, for example, by a strip chart recorder used in conjunction with a YSI Model 2700 Select Biochemistry Analyzer, measuring the amperage (in nanoamps) of analyte samples containing MeOH. The instrument is equipped with a polarographic cell (or cells), such as that shown in FIG. 1 with AOX used as the enzyme. Feed of analyte solutions and buffer solution to the polarographic cell is microprocessor controlled.

Turning specifically to FIG. 3a, nanoamps are continuously recorded on the y axis with the X axis representing time. Feed of MeOH-containing analyte sample is represented at 502. At a predetermined interval after analyte feed, (usually 30 seconds), the analyzer takes a current measurement using this particular measurement to calculate MeOH present in the analyte sample. The time line along which such specific measurement is taken is called the measurement plateau 504, extending between points 504a and 504b. Plateau 504 may be viewed as being a "window" or time slot available in which the analyzer takes the current measurement for use in the MeOH determination calculation. After current measurement has been taken, the cell is purged with buffer solution at a point just downstream from 504b. After such purging, the amperage returns to a lower value.

The microprocessor is set so that a predetermined baseline amperage must be obtained before analyte solution will be fed again. In many instances, return must be made, for example, to a baseline value within ±2.0% of the previous baseline value or the acceptable baseline value could be calculated using a certain percentage taken from the amperage measurement taken along plateau 504, It can be seen that it is desirable that plateau 504 should ideally have a zero slope so that accurate current measurement can be taken at any point in time extending along plateau 504. Unfortunately, in systems such as the aforementioned wherein $CH_2O$ is produced via the enzymatic reaction, it interferes with formation of a horizontal or near zero slope plateau 504. Such is shown in FIG. 3a wherein plateau 504 has a positive slope. This is the type of strip chart profile that is oftentimes generated in MeOH concentration determination systems wherein AOX is used as the enzyme and where it is desired to measure either $O_2$ consumed or $H_2O_2$ produced as a result of the oxidation of MeOH by the enzyme. It is apparent that process conditions producing a plateau 504 having such a positive slope (FIG. 3a) are highly undesirable since current measurement along plateau 504 is not reliable.

In contrast, FIG. 3b represents a desirable strip chart profile of the type seen when PEI is used in the buffer solution to contact the polarographic cell (specifically the enzyme-containing laminated membrane). The PEI serves as a formaldehyde scavenger that inhibits interference with the measurement that would otherwise be caused by the $CH_2O$. In this case, a near zero slope or horizontal plateau 504 is shown indicating improvement in the "window" or time slot available for accurate amperometric measurement of the MeOH analyte. Stated differently, accuracy and reliability of current measurement are improved due to the near constant current measurements existing along the plateau 504. In fact, a slightly negative slope for plateau 504 may be desirable since this would show that $CH_2O$ initially available at commencement point 504a is being removed, in an ongoing manner, from its role as an interferant.

In addition to improvement in the shape of plateau 504 by use of the PEI formaldehyde scavenger in accordance with the invention, another important factor is that the PEI decreases the buffer flushing time normally needed for current measurement to return to an acceptable baseline value. This latter fact is important since the above analyzer, as well as others, will not feed fresh analyte solution for measurement until the acceptable baseline value has been obtained. Accordingly, for those situations in which rapid determination of a multiplicity of analyte-containing sample lots is required, such as those situations encountered by a soft drink bottler attempting to provide quick and accurate "aspartame" concentration levels from a number of sample lots, real savings in time allotted per each analyte sample determination are achieved.

In order to assess the efficacy of the present invention in minimizing $CH_2O$ interference in polarographic measurement methods, the following examples were undertaken. It is to be remembered that the following examples are for purposes of illustration only and should not be construed as being a limitation of the invention.

EXAMPLE 1

Multiple methanol analyte measurements were made using a YSI 2700 Select Biochemistry Analyzer. Each analyte sample contained 54 ppm of methanol, The Enzyme Electrode cells were similar to that shown schematically in FIG. 1. Alcohol oxidass was used as the enzyme. $H_2O_2$ measurement was determined amperometrically with regard to the current generated at the platinum, working anode.

After injection and measurement of the electrical current of each analyte sample by the analyzer, automatic buffer-flushing and calibrations are made to ensure that a desired baseline current is obtained in the enzyme cell before the analyzer feeds another sample to the enzyme electrode cell for current measurement.

Figure 4:
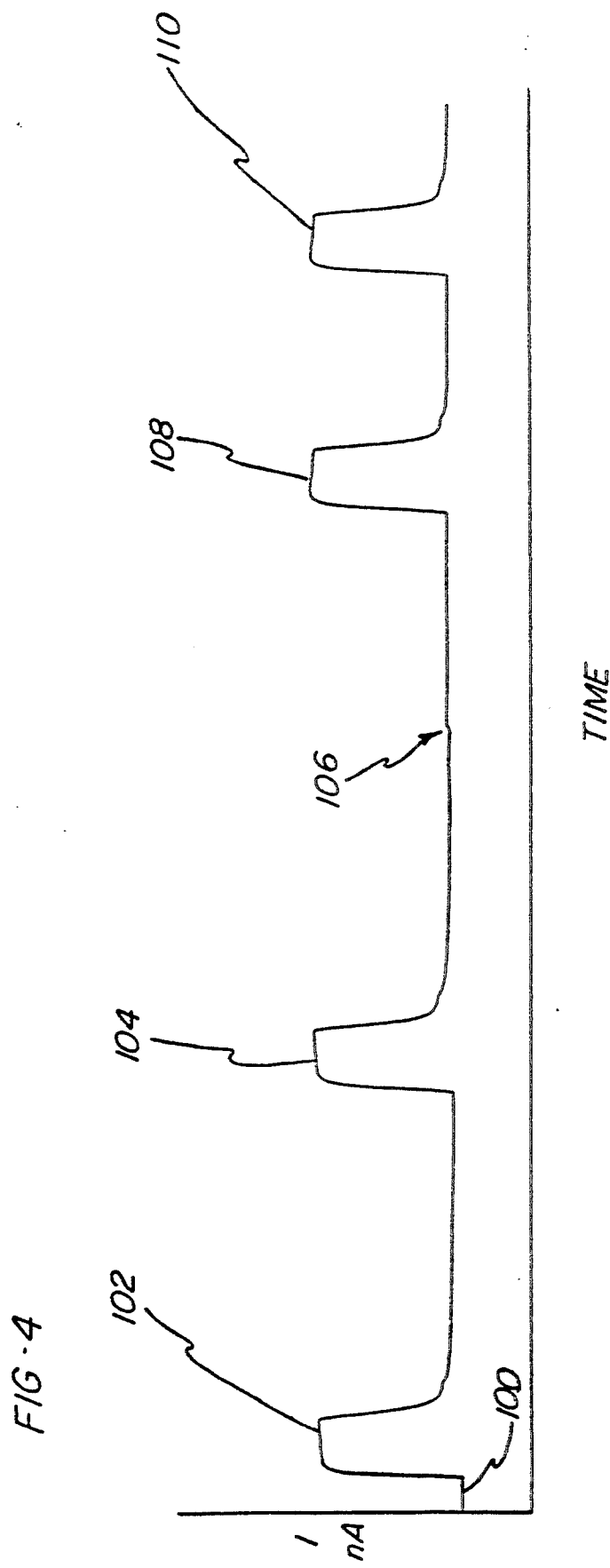
FIG. 4 is a schematic Illustration of a strip chart, similar to that depicted in FIGS. 3a and 3b, comparing current plots obtained when the polarographic cell contains a prior art buffer solution with those obtained with a formaldehyde scavenger containing buffer as reported in Example 1.

FIG. 4 of the drawings provides a schematic illustration of a strip chart generated during this series of tests. (This drawing is not made to scale and is enclosed for illustrative purposes.) X units in FIG. 4 denote time, with Y units signifying current measured in terms of nanoamperes. The analyzer will not feed fresh analyte sample to the enzyme electrode cell until the current measurement in the cell comes within a range of 2.0% of the previous baseline operating current. Here, the starting, designated baseline current was 3.0 nA.

Reference number 100 in FIG. 4 indicates the first injection of 54 ppm methanol to the enzyme cell of the analyzer after the baseline current value had been attained. Electrical current measurement is taken along the plateau region 102 of the drawing. After this measurement, the analyzer automatically flushes the enzyme cell with standard buffer solution, and measures the current at the cell to determine if same has returned to the desired baseline value. If the measurement indicates that the desirable baseline current value has not been obtained, the enzyme cell will then be automatically flushed once again. This process is repeated until the baseline value is obtained.

After measurement 102, eleven flushes were needed before the electrical current of the enzyme cell returned to the acceptable baseline value. The analyzer then fed another analyte containing sample to the cell, with current measurement therefor taken along plateau 104. After measurement 104, the enzyme cell was flushed approximately 8 or 9 times with standard buffer solution without return to the desired baseline current parameter.

As shown at 106, buffer solution containing 500 ppm of 600 m.w. polyethyleneimine was then used as the flushing medium. After approximately three flushes with this PEI containing buffer, desired baseline current was obtained.

Another analyte sample was then automatically fed to the enzyme cell with current measurement made along plateau 108. After this measurement, the cell was automatically flushed with PEI containing buffer. This time only two flushes were required in order to obtain a desirable baseline current before the analyzer fed another analyte containing solution to the test cell for measurement as shown at plateau 110.

In summary, when the standard buffer was used in the test system, many flushes were required before the system could return to steady state base-line current conditions. When PEI was added to the buffer, fewer flushes were required between sample measurements.

EXAMPLE 2

Another set of tests was run to demonstrate how the incorporation of PEI into the instrument buffer affects the response of the AOX electrode to $CH_2O$ which is a substrate for AOX.

Figure 5:
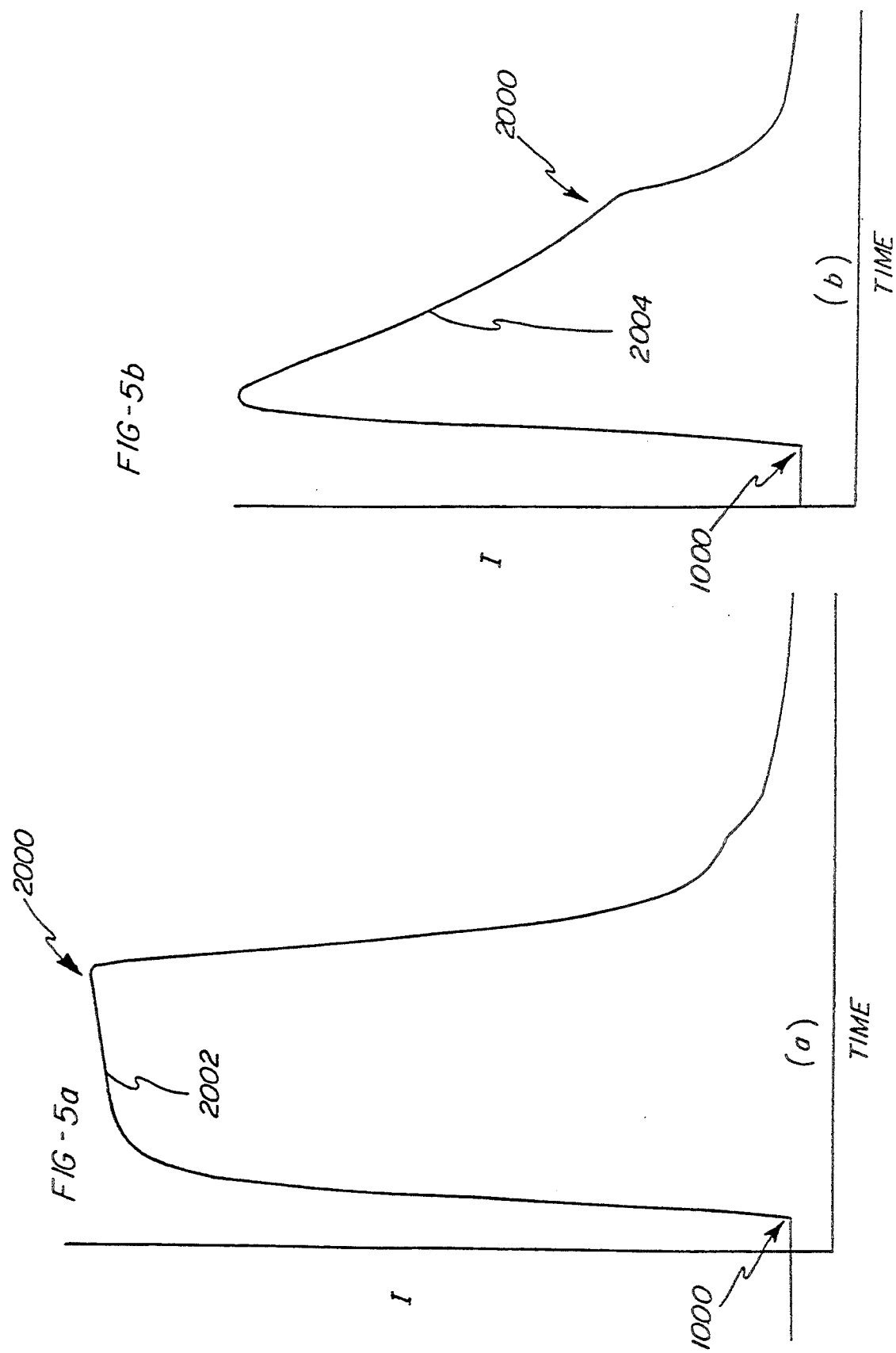
FIG. 5a is a schematic illustration showing current-time measurement of a formaldehyde containing sample in the absence of formaldehyde scavenger as reported in Example 2.
FIG. 5b is a schematic illustration showing current-time measurement of a formaldehyde containing sample wherein the polarographic cell contains a formaldehyde scavenger in accordance with the invention as reported in Example 2.

In accordance with this test, the YSI 2700 Select Biochemistry analyzer was again used as the measurement Instrument. 25 uL samples containing 300 ppm $CH_2O$ solutions were measured: (a) in the absence of PEI, and (b) in the presence of 0.5 g/L, 600 mw PEI. In both cases, the instrument buffer was otherwise the same, pH 9.0, 100 mM carbonate plus sodium chloride, benzoic acid Na salt, dipotassium EDTA, and gentamicin sulfate. In each case, the $CH_2O$ solution was injected at point 1000 as shown in FIG. 5 of the drawings and the system purged with buffer as shown at point 2000.

Results are shown in FIGS. 5a and 5b with FIG. 5a denoting no PEI and 5b illustrating the instant invention with PEI incorporated into the buffer solution. As can be seen in FIG. 5a, when PEI is not used, the slope of the strip chart recording (line 2002), indicative of current measurement when the analyte sample is in contact with the enzyme membrane assembly, is positive indicating the unfavorable kinetics of the interaction of $CH_2O$ with AOX. Conversely, in FIG. 5b, when PEI buffer is used, a rapidly dropping response, or negative slope, is shown along line 2004. This indicates that the PEI is reacting with and removing $CH_2O$ from the solution.

EXAMPLE 3

Figure 6:
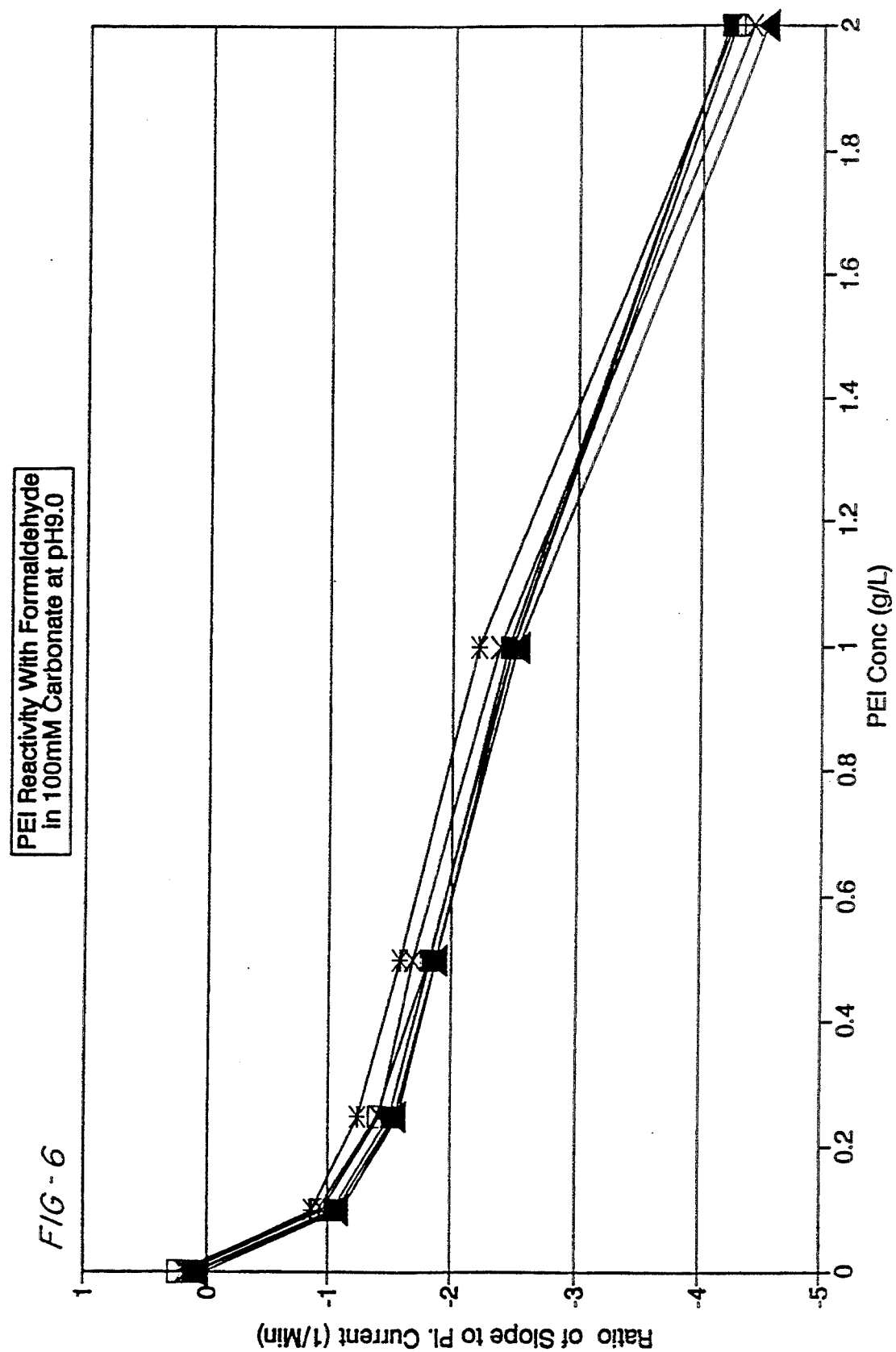
FIG. 6 is a graph showing formaldehyde scavenger reactivity with $CH_2O$ as a function of scavenger concentration present in buffer solutions used to flush the polarographic cell as reported in Example 3.

A series of tests were conducted to assess relative PEI reactivity with $CH_2O$ as a function of PEI concentration in the buffer solution. Responses to 300 ppm $CH_2O$ were determined for each buffer solution as described in Example 2. The ratio of slope to plateau current was used as a measure of relative reactivity to $CH_2O$, Results of these tests are shown in FIG. 6 of the drawings. The plots shown in FIG. 6 are observed response characteristics to 25 uL injections of 300 ppm $CH_2O$ solution determined on each of 6 AOX sensors. The slope of the response curve used to generate the plots shown in the drawing is determined in the last 15 seconds of the 30 seconds between injection and the point where the plateau current is measured: 15 points (1 point/sec) are sampled and a linear regression is performed. The plateau current is measured 30 seconds post injection.

EXAMPLE 4

A series of tests were conducted to assess relative PEI reactivity with $CH_2O$ as a function of buffer pH in 100 mM carbonate buffer. Response to 300 ppm formaldehyde was determined for each buffer solution as described in Example 2. Results of these tests are shown in FIG. 7 of the drawings.

Figure 7:
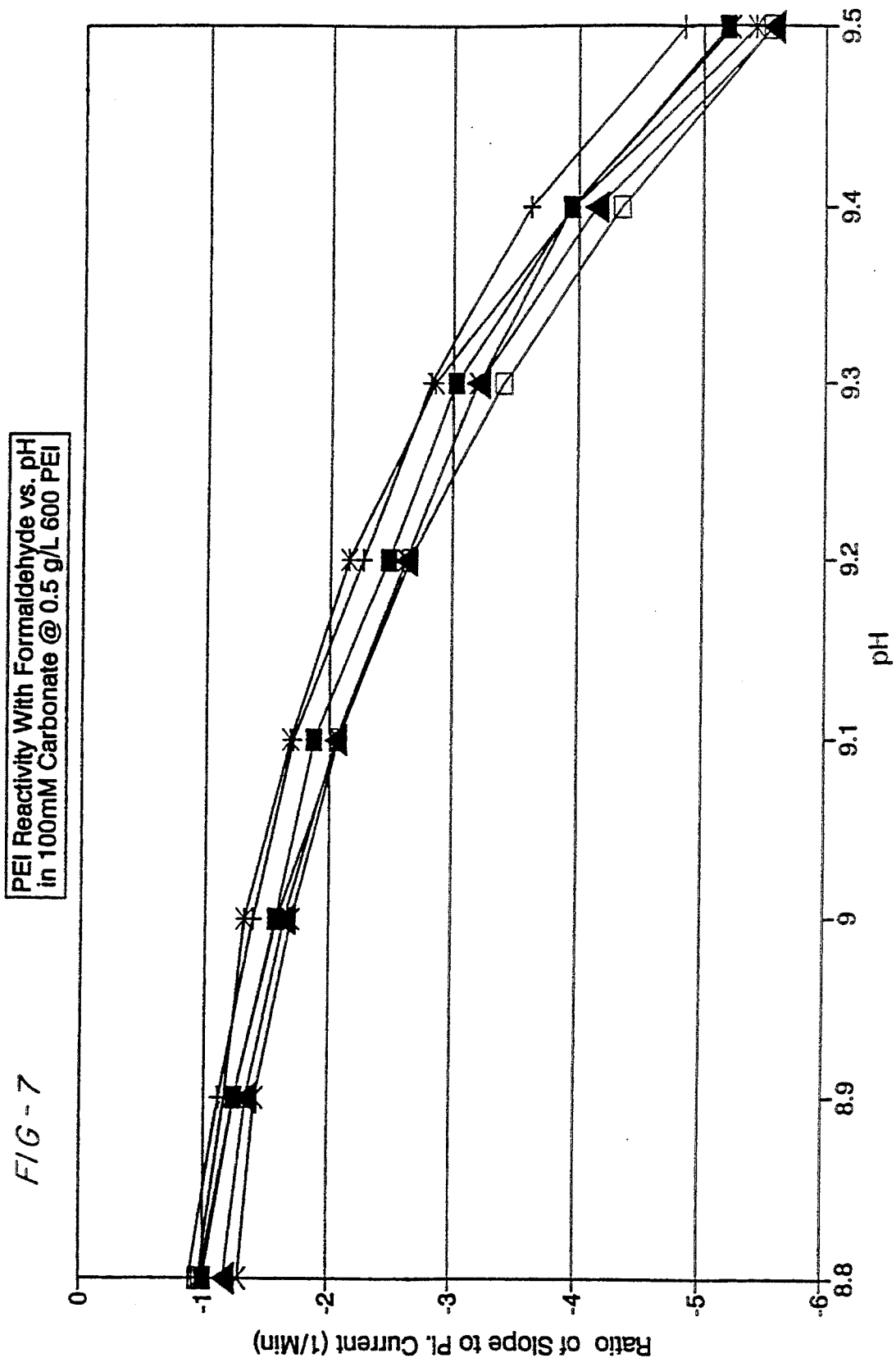
FIG. 7 is a graph showing formaldehyde scavenger reactivity with $CH_2O$ as a function of buffer solution pH as reported in Example 4.

The plots shown in FIG. 7 are response characteristics observed on each of six AOX sensors, All buffer solutions were 0.5 g/L of 600 mw PEI, Other conditions and procedures are set forth above in Example 3.

EXAMPLE 5

(a) Another series of current measurements were undertaken on the YSI 2700 Select Biochemistry Analyzer. This time response curves for alternate injections of 54.3 and 86.9 ppm MeOH in the presence of 0.5 g/L, 600 mw PEI buffer solution were taken. Readings were taken 30 seconds after injection of the MeOH containing analyte sample to the enzyme cell. After each sample injection, the system was cleared with buffer until the final baseline current was less than 2% of the plateau current. A schematic representation of the strip chart generated by these tests is shown in FIG. 8a.

(b) In contrast to the tests performed in Example 5(a), comparative tests were undertaken for alternate injections of 54.3 ppm and 86.9 ppm MeOH in the absence of PEI containing buffer. Process conditions were the same as reported for Example 5(a). A schematic representation of the strip chart generated by these 5(b) tests is shown in FIG. 8b.

(c) Discussion of Example 5 results—Comparison of FIGS. 8a and 8b of the drawings clearly indicates that in the absence of PEI (FIG. 8b) cumulative increases in the baseline current occur upon multiple sample/calibration samples (in comparison to FIG. 8a). This movement in the baseline can adversely affect the accuracy of the measurement. Moreover, as seen in FIG. 8a, less time is shown between measurement plateaus, again showing that when PEI is used, less buffer flushing is needed to obtain an acceptable baseline current before another analyte sample is injected to the enzyme cell for current measurement. In fact, analysis time with PEI buffer is decreased by approximately 30%—allowing about 1.3 times as many analyses per hour to be performed compared to analyses conducted without PEI in the buffer. Accordingly, the amount of buffer solution required for flushing and re-establishing the baseline is decreased about 70%.

EXAMPLE 6

(a) To measure the accuracy of assays made with and without PEI in the buffer solution, a series of test measurements were made on the YSI 2700 Select Biochemistry Analyzer. Successive analyses of known 8.69 ppm and 86.9 ppm MeOH samples were performed. Calibration was made before each analysis using a 54.3 ppm MeOH standard. The volume of sample injected in each case was 25 uL and the result was obtained 30 seconds after analyte sample injection.

Results were obtained by comparing the sample plateau current measured at the designated instrument read time (x seconds after analyte injection—normally 30 seconds) to the plateau current obtained on the calibrator under exactly the same conditions. Any temperature changes are compensated for by adjusting the sample plateau current using an empirically determined correction factor, The sample result is then obtained by dividing the corrected sample plateau current by the calibrator plateau current and then multiplying by the known MeOH concentration of the calibrator (54.3 ppm).

Results are shown in Table 6a.

TABLE 6a

| | Assay Results | | | |
| | Without PEI in Buffer (avg. ± s.d.) | | With PEI in Buffer (Avg. ± s.d.) | |
| Known MeOH Concentration | Measured Concentration | | Measured Concentration | |
| tration | Probe A | Probe B | Probe A | Probe B |
| 8.69 ppm | 7.9 ± 0.2 | 7.5 ± 0.2 | 8.8 ± 0.2 | 8.5 ± 0.2 |
| 86.9 ppm | 87.5 ± 0.9 | 86.8 ± 1.2 | 86.9 ± 0.6 | 86.6 ± 0.5 |

In accordance with Table 6a, it can be seen that PEI in the buffer solution leads to increased accuracy of the MeOH concentration measurements taken with the test instrument. The improved accuracy of the results is seen more clearly in the lower (8.69 ppm) MeOH concentration tests.

(b) Another series of tests were conducted to assess MeOH detection accuracy in systems where $CH_2O$ is added to the analyte containing sample. Test procedures and conditions were the same as used in Example 6(a) except where otherwise noted.

In this series of tests, 54.3 ppm MeOH containing analyte solutions were tested. These analyte solutions also included 50 ppm of formaldehyde. Tests were conducted using buffer solutions with and without 2 g/L PEI therein. A 60 second read time was used in order to allow sufficient time for the PEI to react with the $CH_2O$. Results are reported in Table 6b. Each result is the average of three determinations.

TABLE 6b

| Known MeOH and $CH_2O$ Concentration | Assay Results | | | |
| --- | --- | --- | --- | --- |
| | Without PEI in Buffer (avg. ± s.d.) Measured Concentration | | With PEI in Buffer (Avg. ± s.d.) Measured Concentration | |
| | Probe A | Probe B | Probe A | Probe B |
| 54.3 ppm MeOH and 50 ppm $CH_2O$ | 60.4 ± 0.7 | 66.6 ± 0.7 | 55.2 ± 0.1 | 55.5 ± 0.1 |

It can be seen that the addition of PEI into the buffer improves the accuracy of the MeOH analyte concentration measurement.

In accordance with the patent statutes, the best mode of practicing the invention has been set forth. However, it will be apparent to those skilled in the art that many other modifications can be made without departing from the invention herein disclosed and described.

What is claimed is:

1. A method for measuring methanol concentration wherein a liquid sample is brought into contact with an enzyme to form a polarographically measurable substance and wherein formaldehyde is present as an undesirable interferant in said method, the improvement comprising contacting said formaldehyde with a polyethyleneimine formaldehyde scavenger compound.

2. Method as recited in claim 1 wherein said polyethyleneimine polymer has a molecular weight of between about 200–5,000.

3. Method as recited in claim 1 wherein said formaldehyde is produced by oxidation of said methanol in the presence of alcohol oxidass enzyme.

4. Method as recited in claim 3 wherein said alcohol oxidase enzyme is disposed within a laminated membrane assembly.

5. Method as recited in claim 1 wherein said polyethyleneimine has a molecular weight of between about 200–5,000.

6. A method for determining methanol concentration level in a liquid sample with an enzyme containing laminated membrane assembly wherein an oxidoreductase enzyme is disposed within said laminated membrane and wherein said methanol is placed in contact with said enzyme to form hydrogen peroxide and formaldehyde, the improvement comprising contacting said formaldehyde with a polyethyleneimine polymer having a molecular weight of between about 200 and 1,000,000.

7. Method as recited in claim 6 including the further step of amperometrically measuring the amount of hydrogen peroxide produced.

8. Method as recited in claim 7 wherein said laminated membrane comprises an outer, barrier layer and an inner protective layer with said enzyme being disposed between said outer layer and said inner layer.

9. Method as recited in claim 8 wherein said oxidoreductase enzyme comprises alcohol oxidase.

10. Method as recited in claim 6 wherein said polyalkyleneimine comprises polyethyleneimine having a molecular weight of between about 200–5,000.

11. Method as recited in claim 10 wherein said step of contacting said formaldehyde comprises contacting said formaldehyde with a pH buffer solution containing said polyethyleneimine.

12. Method as recited in claim 11 wherein said polyethyleneimine is present in said buffer solution in an amount of between about 0.0001 to 1000 g/l.

13. Method as recited in claim 12 wherein said polyethyleneimine is present in said buffer solution in an amount of between about 0.1 to 100 g/l and said buffer solution has a pH of about 8–10.

14. Method as recited in claim 13 wherein said polyethyleneimine has a molecular weight of about 600.

15. A method for determining methanol concentration of a methanol containing analyte sample using a polarographic cell having an enzyme containing laminated membrane in close proximity to a working electrode of said cell, wherein said laminated membrane comprises an outer barrier membrane and an inner membrane adjacent said working electrode and wherein said enzyme comprises alcohol oxidase enzyme disposed between said inner and outer membranes, wherein the method comprises the steps of:

(a) contacting the outer membrane of the cell with an analyte sample;

(b) allowing said methanol to pass through said outer barrier layer while inhibiting passage of higher molecular weight species having molecular weights of greater than 1,000,000 through said outer layer;

(c) oxidizing said methanol with said alcohol oxidase to form hydrogen peroxide and formaldehyde;

(d) reacting said formaldehyde formed in said step (c) with an polyethyleneimine formaldehyde scavenger having a molecular weight of between about 200–1,000,000;

(e) allowing said hydrogen peroxide to pass through said inner membrane to gain access to said working electrode while inhibiting passage of compounds having a molecular weight of 200 or greater therethrough, and (f) polarographically measuring hydrogen peroxide present at said working electrode.

* * * * *